United States Patent
Johnson

(10) Patent No.: US 9,561,036 B2
(45) Date of Patent: Feb. 7, 2017

(54) CATHETER LUMEN PARTITIONER

(71) Applicant: RUSH UNIVERSITY MEDICAL CENTER, Chicago, IL (US)

(72) Inventor: Andrew K. Johnson, Chicago, IL (US)

(73) Assignee: Rush University Medical Center, Chicago, IL (US)

(*) Notice: Subject to any disclaimer, the term of this patent is extended or adjusted under 35 U.S.C. 154(b) by 191 days.

(21) Appl. No.: 14/471,289

(22) Filed: Aug. 28, 2014

(65) Prior Publication Data

US 2015/0066072 A1 Mar. 5, 2015

Related U.S. Application Data

(60) Provisional application No. 61/873,509, filed on Sep. 4, 2013.

(51) Int. Cl.
*A61M 29/00* (2006.01)
*A61M 25/00* (2006.01)
*A61B 17/12* (2006.01)

(52) U.S. Cl.
CPC ..... *A61B 17/12031* (2013.01); *A61B 17/1214* (2013.01); *A61B 17/12113* (2013.01);
(Continued)

(58) Field of Classification Search
CPC ................ A61B 17/12031; A61B 17/1214; A61B 17/12113; A61B 2017/1205; A61M 25/0026; A61M 2025/0048; A61M 2025/0034; A61M 2025/0042; A61M 2025/0047; A61M 2025/0046
(Continued)

(56) References Cited

U.S. PATENT DOCUMENTS 5,584,873 A * 12/1996 Shoberg ................ A61N 1/056 607/122
6,527,753 B2 * 3/2003 Sekine ............... A61B 1/00135 600/104
(Continued)

FOREIGN PATENT DOCUMENTS

AU 2012202102 11/2012

OTHER PUBLICATIONS

Search Report issued in European App. No. 14183498.6 (2015).
(Continued)

*Primary Examiner* — Julian W Woo
(74) *Attorney, Agent, or Firm* — Barnes & Thornburg LLP; Alice O. Martin

(57) ABSTRACT

A device and method for treating an aneurysm include a catheter capable of insertion into a body to be positioned adjacent the aneurysm, the catheter including a distal end and an operator end opposite the distal end. The catheter forms a circular pathway extending between the distal end and the operator end. A partitioner extends through the pathway of the catheter, the partitioner being rotatable within the catheter and including one or more lumens that provide an orifice from a first end of the partitioner to a second end of the partitioner. The device further includes a first coil extending through the partitioner from the first end to the second end in a first lumen and a second coil extending through the partitioner from the first end to the second end in a second lumen. The first and second lumens may be fully circumscribed by the partitioner and have first and second diameters, respectively.

5 Claims, 8 Drawing Sheets

(52) U.S. Cl.
CPC . *A61M 25/0026* (2013.01); *A61B 2017/1205* (2013.01); *A61M 2025/0034* (2013.01); *A61M 2025/0042* (2013.01); *A61M 2025/0046* (2013.01); *A61M 2025/0047* (2013.01); *A61M 2025/0048* (2013.01)

(58) Field of Classification Search
USPC .......................................... 604/164.09, 171
See application file for complete search history.

(56) References Cited

U.S. PATENT DOCUMENTS

| | | | | |
|---|---|---|---|---|
| 7,130,700 | B2* | 10/2006 | Gardeski | A61M 25/0021 604/171 |
| 8,328,860 | B2* | 12/2012 | Strauss | A61B 17/12022 623/1.11 |
| 9,289,266 | B2* | 3/2016 | Weitzner | A61B 1/0014 |
| 2003/0191425 | A1 | 10/2003 | Rosenblatt et al. | |
| 2009/0182200 | A1 | 7/2009 | Golden et al. | |
| 2012/0283764 | A1 | 11/2012 | Solar et al. | |

OTHER PUBLICATIONS

Chalouhi et al., "Is Packing Density Important in Stent-Assisted Coiling?" *Neurosurgery*, 71(2): 381-387 (2012).
Guglielmi et al., "Electrothrombosis of saccular aneurysms via endovascular approach. Part 1: Electrochemical basis, technique, and experimental results," *J. Neurosurg.*, 75:1-7 (1991).
Guglielmi et al., "Electrothrombosis of saccular aneurysms via endovascular approach. Part 2: Preliminary clinical experience," *J. Neurosurg.*, 75:8-14 (1991).
Slob et al., "Coil thickness and packing of cerebral aneurysms: a comparative study of two types of coils," *AJNR Am J Neuroradiol.*, 26:901-903 (2005).
Sluzewski et al., "Packing performance of helical Guglielmi detachable coil (GDC) 18 in intracranial aneurysms: a comparison with helical GDC 10 coils and complex Trufill/Orbit coils," *AJNR Am J Neuroradiol.*,28:1384-1387 (2007).
U.S. National Institutes of Health clinical trials registry, "Study of the Penumbra Coil 400 System to Treat Aneurysm (ACE)," http://clinicaltrials.gov/ct2/show/NCT01465841. Oct. 28, 2011. Accessed May 15, 2012.

* cited by examiner

CATHETER LUMEN PARTITIONER

CROSS REFERENCE TO RELATED APPLICATIONS

This application claims the benefit of priority under 35 U.S.C. §119(e) to U.S. Provisional Patent Application No. 61/873,509, filed Sep. 4, 2013. The disclosure set forth in the referenced application is incorporated herein by reference in its entirety.

BACKGROUND

A catheter lumen partitioner and methods for treating aneurysms, traumatic fistulae, and/or tumor embolizations are disclosed. In particular, a catheter lumen partitioner may be used in conjunction with a coil delivery system for delivering coils to the location of an aneurysm to be treated.

Devices for delivering and deploying an embolization coil in the treatment of aneurysms are known in the industry. Occluding devices such as embolization coils have been used to stop undesired blood flow. For instance, introduction of embolization coils in the location of an aneurysm reduces the flow of blood and permits/promotes the natural clotting-formation process to occur. Such coils may be made of any suitable material that is compatible with a patient's biology and suitable to be maintain its structural integrity while in the patient's body. Coils for embolization of aneurysms have retained the largest share of the global neurointervention market that is worth over $1 billion annually. Endovascular treatment of aneurysms continues to improve and the non-invasive nature and rapid procedure recovery has made endovascular aneurysm treatment much more popular than surgical aneurysm treatment.

Aneurysm coiling is not a perfect science, however, as the distribution of coil material within an aneurysm is not uniform. In addition, aneurysm treatment may be limited to the use of only a single coil if there is difficulty or safety issues with placing an additional coil within the aneurysm after a first coil has been placed. Thus, aneurysm treatment may not be optimized.

SUMMARY

A new and unique way of partitioning a larger microcatheter is disclosed wherein lumen(s) of the catheter are appropriately sized for coils that may be of various sizes. The catheter lumen partitioner may be positioned inside a catheter prior to insertion of a coil near the aneurysm site, or it may be positioned inside a catheter after the catheter has already delivered a first coil to near the aneurysm site, in order to deliver a second coil to the aneurysm site. The lumen partitioner may also be positioned inside a catheter in order to deliver two or more coils to the aneurysm site at the same time.

In one embodiment, the partitioner may concentrically narrow the lumen of the catheter for receiving, guiding and delivering a smaller coil to the lesion area. The lumen may include a diameter that is varied in size in proportion to the catheter and may correspond to the diameter of the smaller coil being received, guided or delivered. In various illustrations, the partitioner may extend from the lumen to an interior surface of the catheter, or the partitioner may extend through only a portion of the space between the lumen and the interior surface of the catheter. In still another embodiment, the partitioner adjacent a first end of the catheter may provide one or more guiding components adjacent the lumen for placement of a coil into the lumen.

In a second embodiment, the partitioner creates multiple smaller lumens for simultaneously receiving, guiding and delivering multiple smaller coils to the lesion area. The multiple lumens may be of similar or varied diameter to each other, and may extend through lumens of similar or varied diameter. The multiple lumens may be eccentrically positioned about the interior of the catheter.

In a third embodiment, the partitioner is eccentric in the catheter and allows the operator to twist the coil wire and the partitioner using torque to adjust the entry position of a coil into the region of an aneurysm or existing coil mass.

Other embodiments of the catheter lumen partitioner are also envisioned.

DETAILED DESCRIPTION

Figure 1:
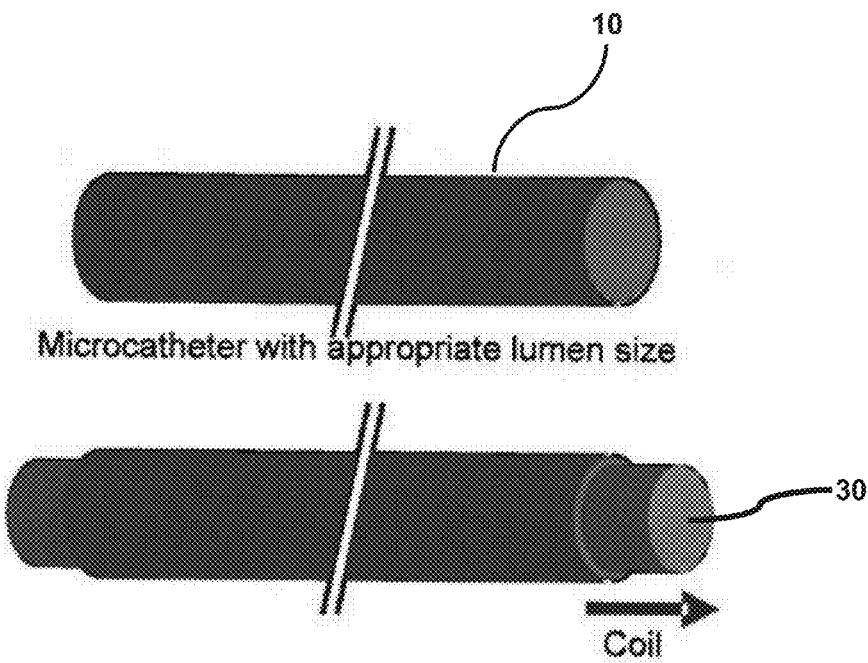
FIG. 1 shows a diagrammatic view of customary catheter (black) with a coil (gray) being delivered through a lumen of the microcatheter.
Figure 2:
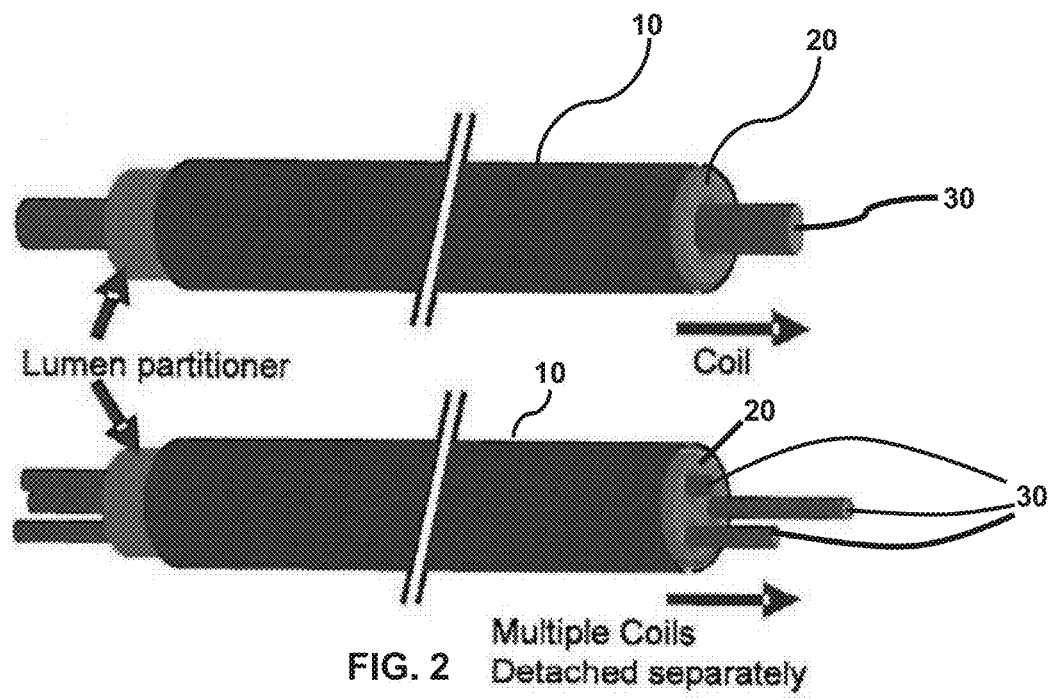
FIG. 2 shows embodiments of a catheter with a single-lumen partitioner and a catheter with a multiple-lumen partitioner, the partitioners extending through the catheters (black) with coil(s) (gray) extending through the partitioners

Treatment of an aneurysm or similar embolism requires resisting or preventing the flow of fluid within a relatively confined space. Often, a porous medium may be used to block or prevent such fluid flow. However, resistance to flow of fluid across a porous medium is affected by several attributes of both the fluid and the porous medium. In coiling aneurysms, use of coils of different sizes may be the optimal method to resist fluid flow in different situations. For instance, a combination of coil sizes may be the most effective way to eliminate flow through an aneurysm. The Kozeny-Carman equation and Darcy's Law in relationship to aneurysm coiling are described herein.

Based on the equation, larger coils have a significant advantage in their ability to increase coil packing density and decrease the residual volume of the aneurysm—thereby decreasing porosity in the equation. Large coils may also be more resistant to compaction within an aneurysm. Smaller coils have the key advantage of decreasing the equivalent channel diameter when packed at an equal density to larger coils. Smaller coil diameter leads to smaller adjacent channels for flow. Smaller coils also have the advantage of fitting and folding more easily into the aneurysm when packing density is already high.

In light of the advantages for larger and smaller coils, an ideal system for coiling involves first using large coils to create a sturdy frame for the coil mass and to quickly decrease porosity. Thereafter, smaller and smaller coils may be introduced to maximize packing density (decrease porosity) and to minimize the equivalent channel diameter.

The current disclosure describes a coil delivery device, such as a catheter (10), that could greatly improve the success of coiling to treat aneurysms. Treatment of aneurysms with coils (20) of multiple sizes, instead of the current trend of using coils of very similar sizes, could make such a device invaluable to save time and save money in preventing the use of additional microcatheters. Instead, a single catheter (10) may be used to deliver multiple coils of varying sizes.

Use of various sizes of coils provides an efficient means to pack or prevent fluid flow near an aneurysm, for example. An article by Chalouhi et al. explored the importance of coil packing density in stent-assisted embolization.[1] There is overwhelming evidence that increased coil packing density improves the probability of aneurysm occlusion, but reliance on this variable in isolation when using multiple types of coils may generate misleading results.

Several permutations of the original 0.010 inch diameter Guglielmi detachable coil design have been produced since the original was presented in 1991.[2,3] Among size, shape, stiffness, and length modifications, alteration of coil diameter has become a popular method for increasing coil packing density within an aneurysm and presumably aiding effective aneurysm occlusion. Trufill (0.012 inch, Cordis, Miami Lakes, Fla.), GDC 18 (0.0135-0.015 inch, Stryker, Fremont, Calif.), and Penumbra Coil 400 (0.020 inch, Penumbra, Alameda, Calif.) have been, or are currently, being studied with respect to coil packing density.[4-6] However, coil packing density may be inadequate for evaluation of aneurysm treatment when coil diameter varies.

Darcy's law and the Kozeny-Cannan equation may be applied to aneurysm coiling. Darcy's law, presented by Henry Darcy in 1856, is used to evaluate the flow or pressure drop of a liquid across a uniform, porous medium with known permeability.[7] The Kozeny-Carman equation for permeability of porous media is credited to Josef Kozeny who proposed it in 1927 and Carman who later modified it.[8,9] When the Kozeny-Carman equation for permeability is applied, Darcy's law takes the form $$\frac{\Delta p}{L} = \frac{180 \overline{V}_0 \mu}{\Phi_s^2 D_p^2} \frac{(1-\epsilon)^2}{\epsilon^3}$$

where $\Delta p$ is pressure drop, L is the length of the porous medium, $V_0$ is the average velocity of fluid at the porous medium cross-section, $\mu$ is the viscosity, $\epsilon$ is the porosity, $\Phi_s$ is the sphericity of filling elements which comprise the porous medium, and $D_p$ is the average filling element diameter.

Flow through an aneurysm is complex and coil packing within an aneurysm is certainly not uniform, but the principles of Darcy's law and the Kozeny-Carman equation apply. Blood viscosity ($\mu$) and velocity at the aneurysm neck ($V_0$) are variables intrinsic to the patient. Length (L) is complex in an aneurysm model as the path of bulk blood flow through the aneurysm is tortuous and likely changes through the duration of the pulse. This should be relatively constant when comparing coiling techniques in identical aneurysms. The sphericity constant ($\Phi_s$) of a coil is approximated by that of a long cylinder and varies negligibly with coil diameter. This constant is inversely proportional to surface area to volume ratio, so coils with variations that increase surface area will decrease $\Phi_s$, thus increasing pressure drop across the coil mass.

Holding other variables constant, many investigations have convincingly shown that increasing packing density, which decreases porosity ($\epsilon$), decreases flow through aneurysms and improves occlusion rates. However, the importance of coil diameter (D) to the filtration/permeability equation has been overlooked when comparing coils of different diameter and using packing density to measure results. Particle diameter ($D_p$) is approximated by the coil diameter (D), and the Kozeny-Carman equation implies that pressure drop is inversely proportional to its square.

Figure 15C:
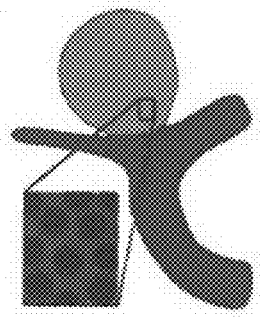
FIG. 15 shows diagrammatic examples of 50% packing density of particles in a two-dimensional aneurysm model, including (A) two particles whose diameters are half that of the aneurysm to achieve 50% packing density, (B) multiple intermediate size particles providing exactly 50% packing density, and (C) multiple particles smaller than a red blood cell that would unquestionably eliminate blood flow with 50% packing density.
Figure 15B:
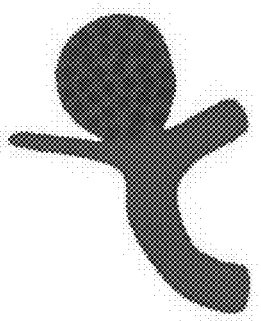
Figure 15A:
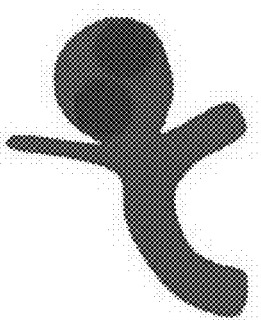

Simply put, larger coils leave a larger equivalent channel diameter for blood flow between them. Thus, when packing density is constant, coils with a smaller diameter will be much more effective at stopping flow into and through the aneurysm. A visual example of extremes demonstrating this concept is provided in FIG. 15.

Several features of larger coils are still appealing, including better formation of a coil frame within the aneurysm, resistance to coil compaction, and faster volume reduction of the aneurysm. Yet, the ability to achieve equivalent coil packing density should not be counted among them. Packing density is an unreliable method of comparing coils of different diameters. The ideal coil diameter for aneurysm embolization is likely to be situation dependent. Similar to the way beavers dam a river, optimal embolization may depend on a combination of coil sizes. Variability of coil selection likely did not affect the results provided by Chalouhi et al., and again, this publication provides insight into the effect of stents in aneurysm treatment.

Therefore, use of multiple coils having multiple diameters is beneficial in effectively addressing and treating aneurysms. Coil diameters sizes may be standardized across the industry, while coils of various diameters may be combined together to provide an optimal combination based on a particular patient's needs.

The current disclosure demonstrates a catheter partitioner (20) that allows smaller diameter coil(s) (30) to be inserted through a microcatheter (10) designed for larger diameter coil(s) (30). In such a way, coils of multiple diameters may be placed near an aneurysm through a single catheter, reducing the time, resources, and potential issues associated with use of multiple catheters to place multiple coils. The partitioner (20) may be suspended or exist in irrigation or fluid (not shown) inside the catheter (10) to permit movement or rotation of the partitioner (20) within the catheter (10). This irrigation may be continuously around and/or within the partitioner (20). Other forms of irrigation are widely known in the industry and are also envisioned.

Figure 3:
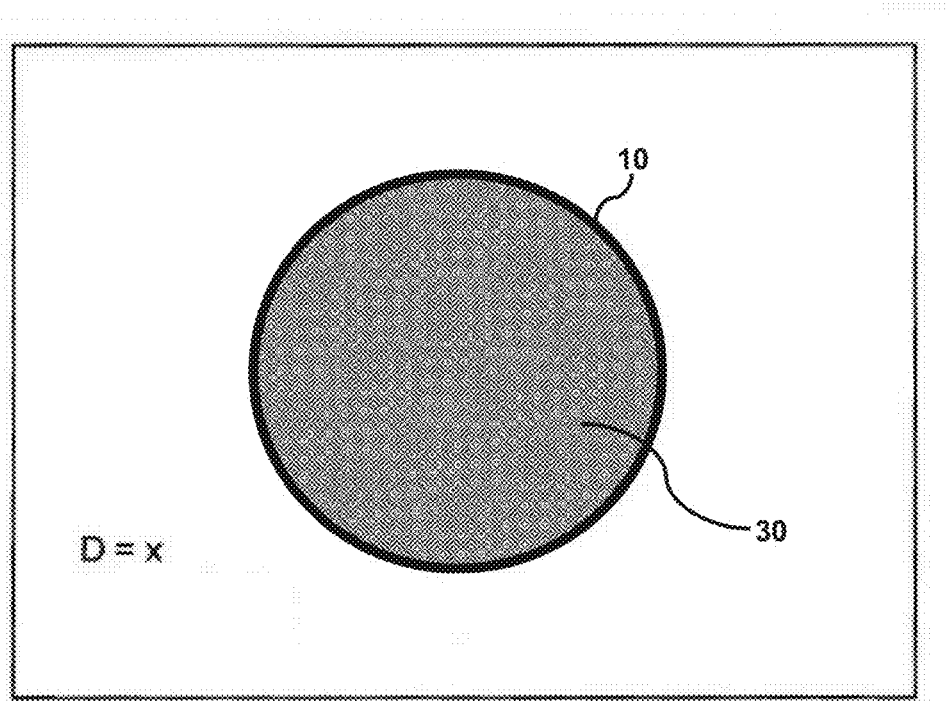
FIG. 3 shows a diagrammatic cross-sectional view of customary catheter (black) with a coil (gray) being delivered through the lumen of the microcatheter.

This concept is illustrated in the Figures. FIG. 1 and FIG. 3 show a customary catheter (10) (black) with a coil (30) (gray) being delivered through the lumen of the catheter. FIG. 2 and FIGS. 4-13 show various catheter partitioners (20) extending through the catheter to allow delivery of one or more coil(s) (30) with varying or smaller diameters within the same catheter (10). In illustrative embodiments, the partitioner (20) may be similar to a second, smaller-diameter catheter that is insertable into or nests within the catheter (10). In other illustrative embodiments, the diameter (D) of the coil(s) (30) may be anywhere between 5mm and 24 mm.

In various embodiments, the partitioner (20) may extend from the distal end of the catheter (10) (inside the body) to the operator end of the catheter (10) so that the operator can push coils through the partitioner and catheter to the target lesion or aneurysm. In illustrative embodiments, the coil may be attached to a wire or other injection means at the operator end of the catheter, the wire configure to push the coil through the partitioner and out the distal end of the catheter and may be electronically detached therefrom once the coil is in place. Other methods for pushing the coil through the partitioner and/or detaching the coil from the injection wire or similar means are well known in the industry.

Figure 8:
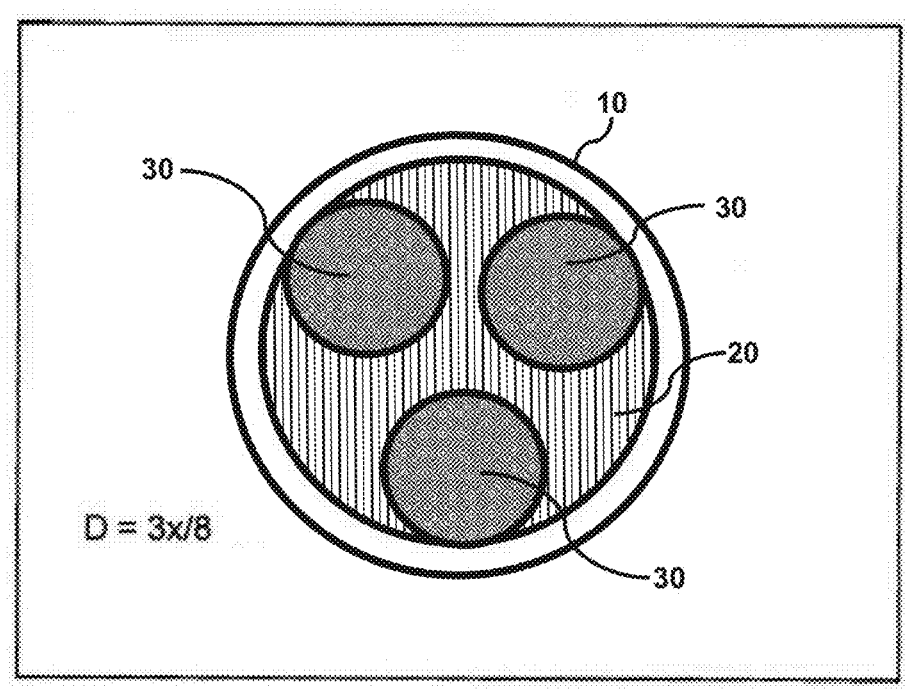
FIGS. 8-13 show various embodiments of a catheter with a multiple-lumen partition and multiple coils extending therethrough.
Figure 9:
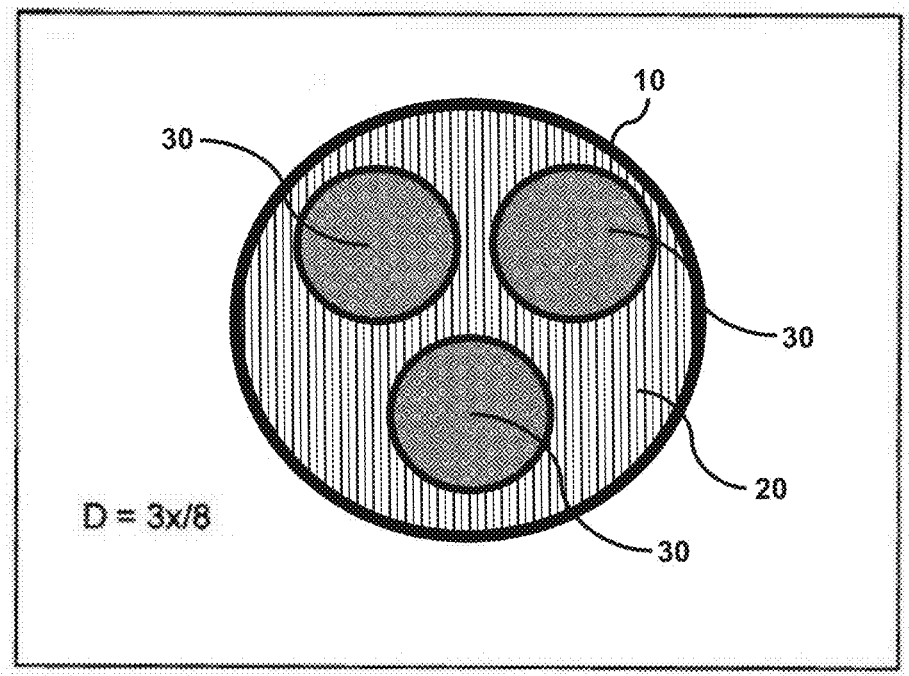
Figure 10:
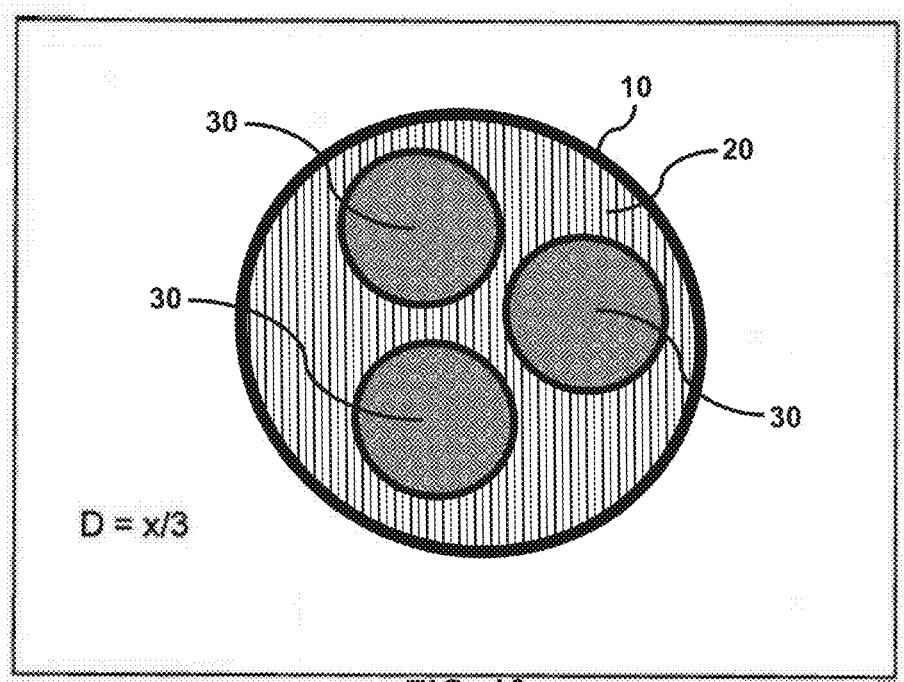
Figure 11:
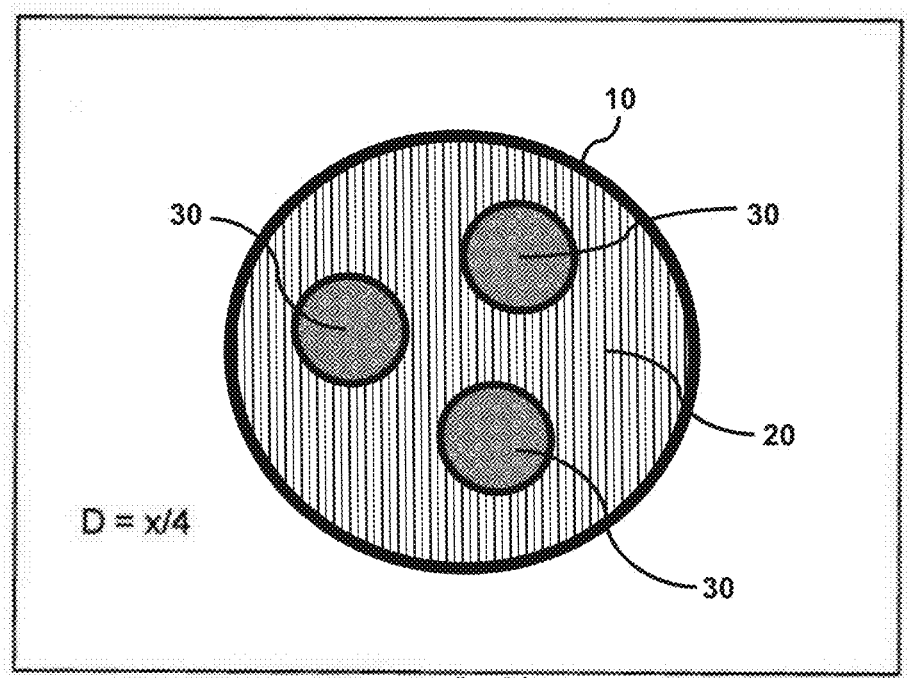
Figure 12:
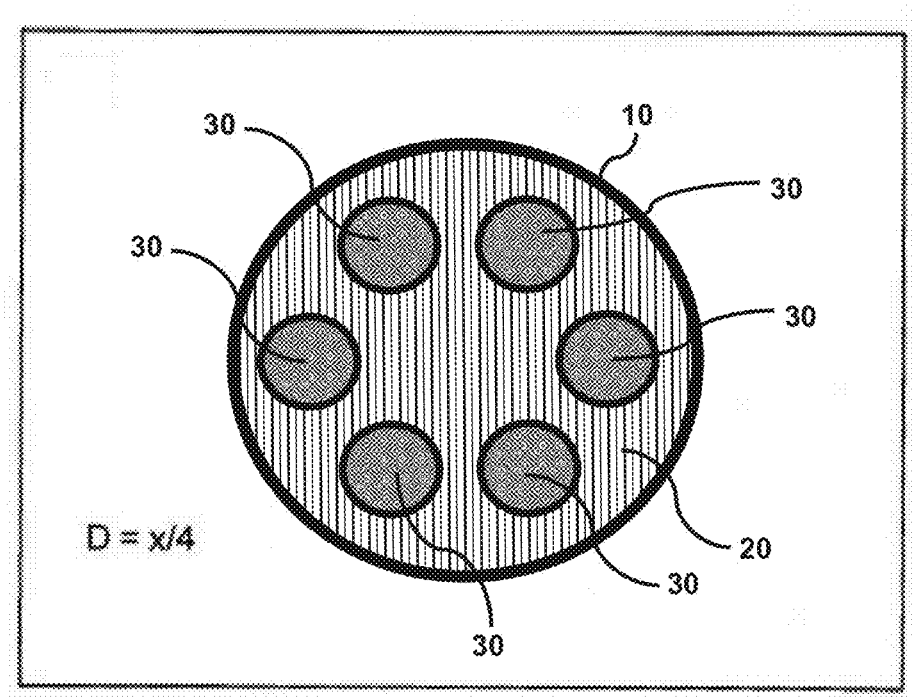
Figure 13:
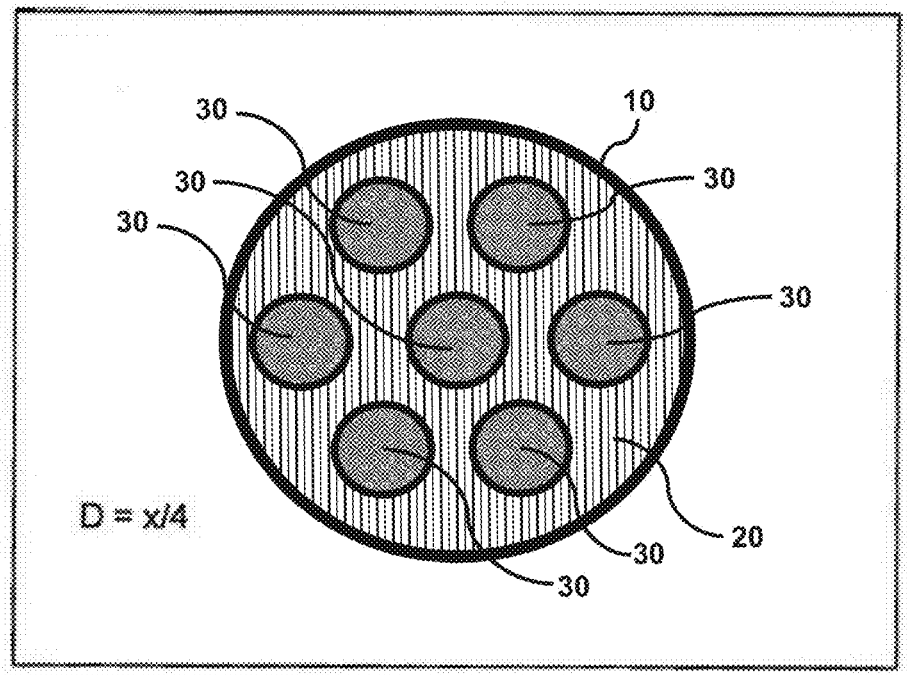

In other embodiments, the partitioner adjacent the operator end of the catheter may provide one or more guiding components into the lumen for aligning/inserting a coil within the lumen. The guiding component may be a depression or shaped as a funnel. In other embodiments, the partitioner may not fully surround the coil within the catheter, as shown in FIG. 8, or the coil may be partially encompassed by an interior surface of the catheter. Such a design may provide for a reduction in the required catheter (10) size and/or in a reduction of the amount of materials required to produce the catheter (10) or partitioner (20).

Figure 4:
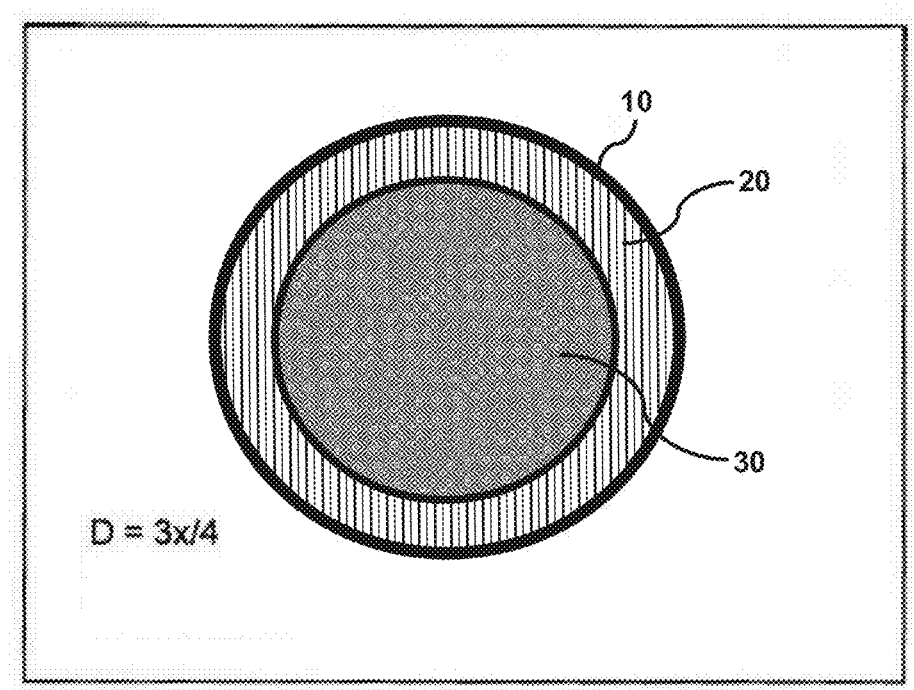
FIGS. 4-7 show various embodiments of a catheter with a single-lumen partition and a coil extending therethrough.
Figure 5:
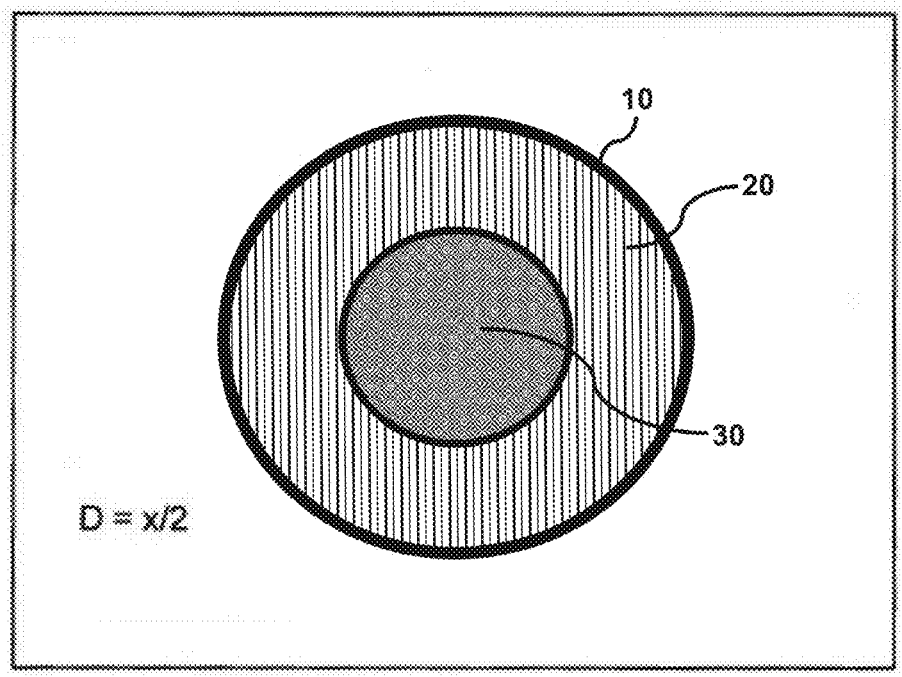
Figure 7:
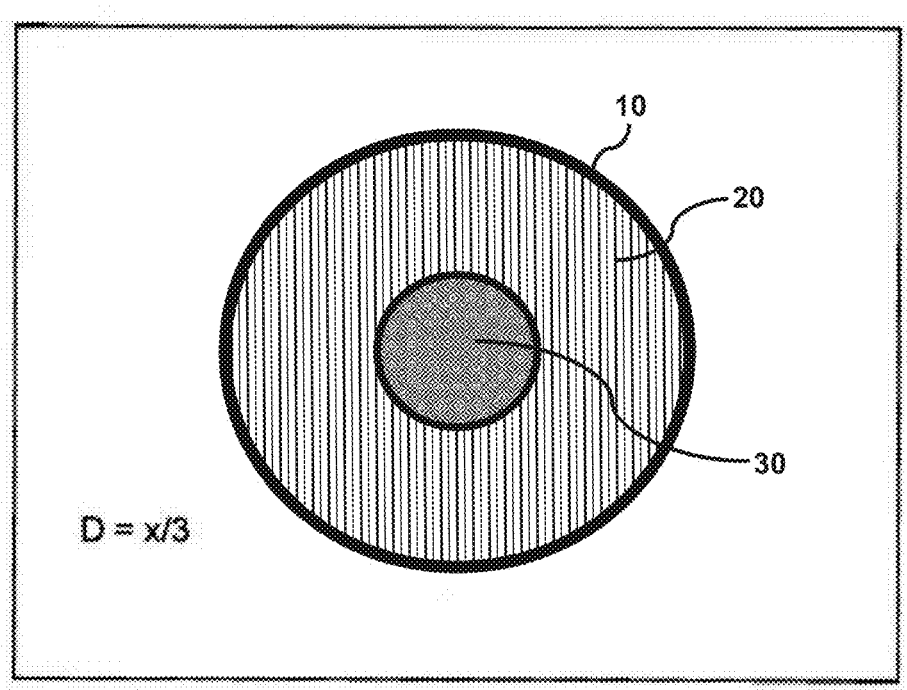

In illustrative embodiments, FIGS. 4, 5 and 7 show a sheath-like partitioner (20) that effectively narrows the lumen of the catheter (10) concentrically to provide an appropriate sized lumen for smaller coils (30).

Figure 6:
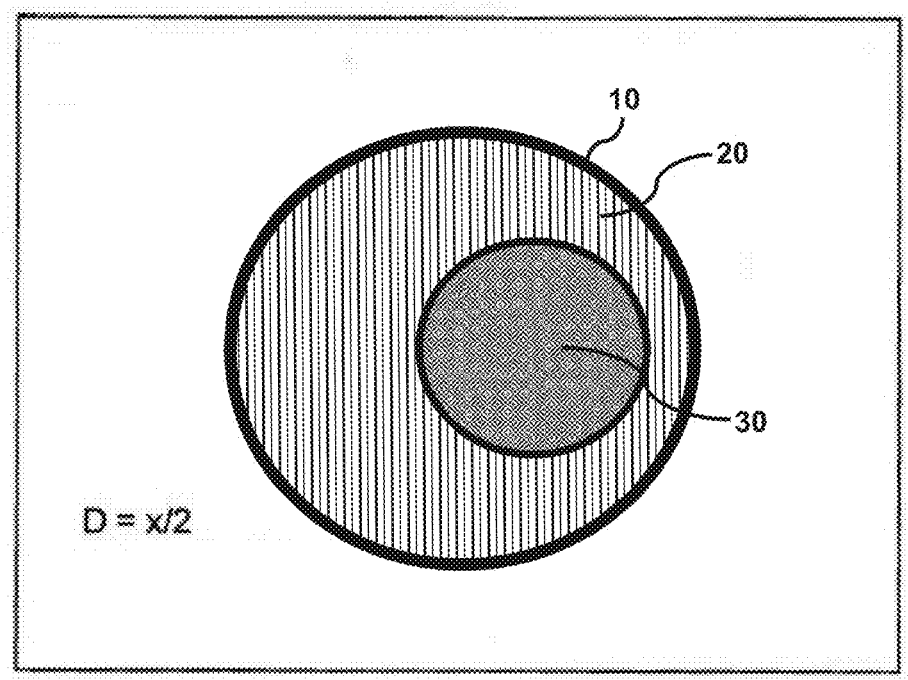

FIG. 6 shows a partitioner (20) that creates an eccentric lumen of the catheter (10), a feature which could allow the operator to have better control during coiling with torque of the partitioner/coil pushing wire. Specifically, a coil being ejected from the partitioner may meet resistance at or near the aneurysm location, particularly from other existing coils in the area. The coil ejection from the partitioner may be random in nature and masses already in the area may impede delivery of the coil. An eccentric lumen permits an operator to turn/twist the partitioner and coil within the catheter by rotating the partitioner to move the delivery location of the ejecting coil. Because of the eccentric nature, the coil being delivered may encounter less resistance after being moved to a different delivery location.

FIGS. 8-13 demonstrate different embodiments of a multiple-lumen partitioner (20) in a catheter (10). Such a device would allow simultaneous introduction of more than one coil (30) through a single catheter (10). This could effectively serve the purpose of the "double catheter" technique for coiling. It would also allow more efficient coiling, eliminating some of the time required for removal of coil wires and insertion of new coils.

Figure 14:
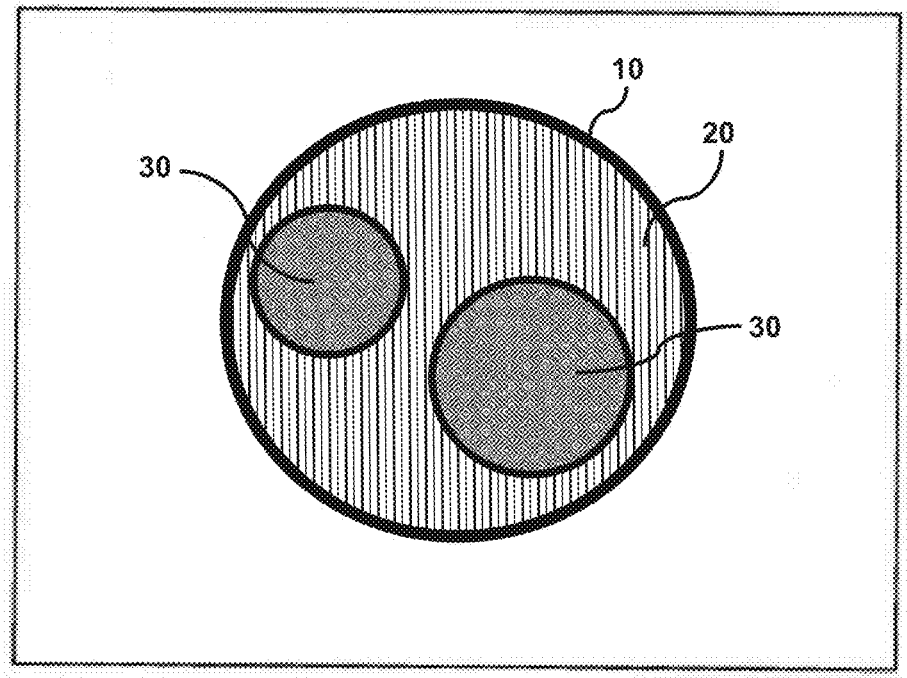
FIG. 14 shows an alternative embodiment of a catheter with a multiple-lumen partition with eccentric or offset lumens and multiple coils extending therethrough.

FIG. 14 shows another variant where a multiple-lumen partitioner (20) allows coils (30) of two different sizes to be inserted into a single catheter (10) simultaneously and/or eccentrically.

The figures are provided for illustrative purposes and are not intended to limit the scope of the disclosure.

PUBLICATIONS

The following publications are incorporated by reference to the extent they relate materials or methods disclosed herein.
1. Chalouhi N, Dumont A S, Hasan D, et al. Is Packing Density Important in Stent-Assisted Coiling? *Neurosurgery*. 2012. doi: 10.1227/NEU.Ob013e31825c36dd.
2. Guglielmi G, Vinuela F, Sepetka I, Macellari V. Electrothrombosis of saccular aneurysms via endovascular approach. Part 1: Electrochemical basis, technique, and experimental results. *JNeurosurg*. 1991; 75:1-7.
3. Guglielmi G, Vinuela F, Dion J, Duckwiler G. Electrothrombosis of saccular aneurysms via endovascular approach. Part 2: Preliminary clinical experience. *J Neurosurg*. 1991; 75:8-14.
4. Slob M J, van Rooij W J, Sluzewski M. Coil thickness and packing of cerebral aneurysms: a comparative study of two types of coils. *AJNR Am J Neuroradiol*. 2005; 26:901-903.
5. Sluzewski M, van Rooij W J. Packing performance of helical Guglielmi detachable coil (GDC) 18 in intracranial aneurysms: a comparison with helical GDC 10 coils and complex Trufill/Orbit coils. *AJNR Am J Neuroradiol*. 2007; 28:1384-1387.
6. U.S. National Institutes of Health clinical trials registry. Study of the Penumbra Coil 400 System to Treat Aneurysm (ACE). http://clinicaltrials.gov/ct2/show/NCT01465841. Oct. 28, 2011. Accessed May 15, 2012.
7. Darcy H. Les Fontaines Publiques de la Ville de Dijon. Paris: Dalmont; 1856.
8. Kozeny J. Ueber kapillare Leitung des Wassers im Boden. *Sitzungsber Akad Wiss*. 1927; 136:271-306.
9. Carman P C. Fluid flow through granular beds. *Transactions, Institution of Chemical Engineers*. 1937; 15:150-166.

The invention claimed is:

1. A method of treating an aneurysm, the method comprising:
   providing a first catheter directed to a location of the aneurysm, the first catheter having a first lumen for coil delivery, and the first lumen having a first lumen diameter;
   (a) inserting a first coil or coils into the first catheter, the first coil(s) having a first coil diameter;
   (b) delivering the first coil(s) through the first catheter to the location of the aneurysm, the first coil(s) exiting the first catheter and forming a first coil frame at the location of the aneurysm;
   (c) providing a second catheter or partitioner, which nests within the first catheter, the second catheter or partitioner having a second lumen that has a second lumen diameter that is smaller than the first lumen diameter, the second catheter or partitioner also directed to a location of the aneurysm;
   (d) inserting a second coil into the second lumen of the second catheter or partitioner, the second coil having a second coil diameter that is smaller than the first coil diameter; and
   (e) delivering the second coil through the second catheter to the location of the aneurysm, the second coil exiting the second catheter and forming a second coil frame at the location of the aneurysm.

2. The method of claim 1, wherein the first coil frame and second coil frame block flow of fluid into the aneurysm.

3. The method of claim 1, wherein the first coil and second coil are delivered by a coil pushing wire.

4. A method of treating an aneurysm, the method comprising:
   (a) providing a partitioner in an existing coil-delivery catheter directed to a location of the aneurysm, the partitioner including multiple lumens;
   inserting a first coil into one of the lumens of the partitioner of the catheter, the coil having a first coil diameter;

inserting a second coil into a second one of the lumens of the partitioner of the catheter, the second coil having a second coil diameter that is equal to or smaller than the first coil diameter; and delivering the first coil through the catheter to the location of the aneurysm to form a first coil frame at the location of the aneurysm, and delivering the second coil through the catheter to the location of the aneurysm to form a second coil frame at the location of the aneurysm.

5. The method of claim 4, wherein the first coil and second coil are delivered to the location of the aneurysm simultaneously.

\* \* \* \* \*